United States Patent [19]

Lider et al.

[11] Patent Number: Plant 6,166

[45] Date of Patent: May 3, 1988

[54] HYBRID GRAPEVINE ROOTSTOCK

[75] Inventors: Lloyd A. Lider; Harold P. Olmo, both of Davis; Austin C. Goheen, Winters, all of Calif.

[73] Assignee: The Regents of the University of California, Berkeley, Calif.

[21] Appl. No.: 866,536

[22] Filed: May 23, 1986

[51] Int. Cl.[4] ..... A01H 5/03

[52] U.S. Cl. ..... Plt./47

[58] Field of Search ..... Plt./47

*Primary Examiner*—Robert E. Bagwill

*Attorney, Agent, or Firm*—Townsend and Townsend

[57] ABSTRACT

A new and distinct variety of grapevine rootstock is provided. It is characterized by its immunity to feeding by the nematode vector of grapevine fanleaf virus and to feeding by phylloxera. When grafted with scion cultivars, such as 'Cabernet Sauvignon,' 'Chenin blanc,' and 'Carignane,' the variety may be planted in soil contaminated with viruliferous nematodes and/or phylloxera and will produce healthy fruit and excellent yields.

1 Drawing Sheet

The present invention relates to a new and distinct rootstock variety of grapevine. More particularly the new variety, which has been named 'VR 039-16,' has been shown to effectively tolerate grapevine fanleaf virus and *Xiphinema index*, the nematode vector.

Figure 1:
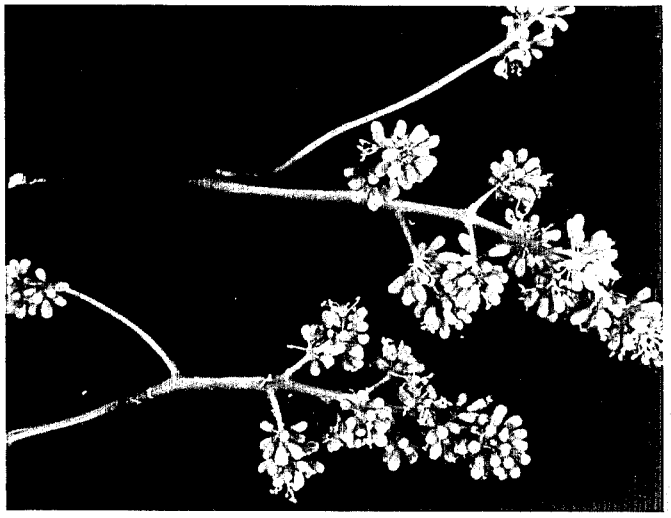

FIG. 1 shows a typical flower cluster form of the new variety.

Figure 2:
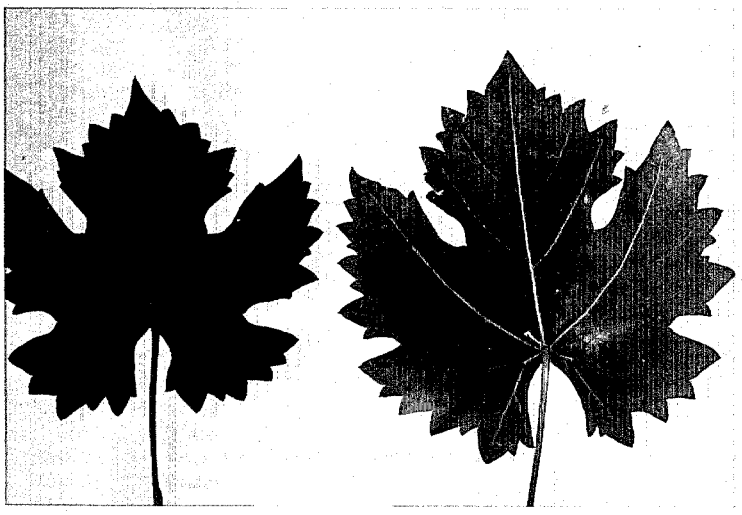

FIG. 2 typifies the mature leaves of the new variety.

Figure 3:
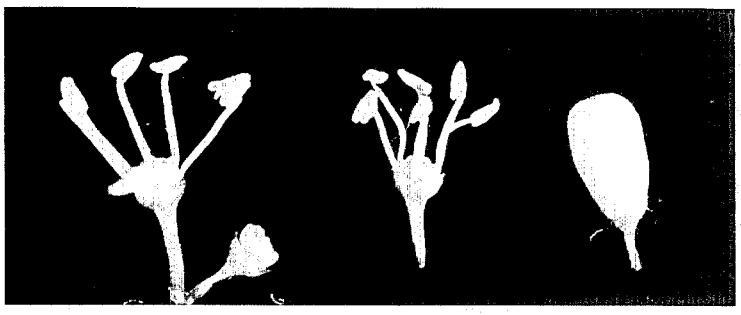

FIG. 3 shows the flowers of the new variety.

A serious problem which has faced the California grape industry for many years is the grapevine fanleaf virus — *Xiphinema index* nematode complex. Soil fumigation treatments have had limited success in controlling the vector spreading infectious degeneration. Frequently soil treatment has completely failed. When planted in soil infested with viruliferous *X. index, Vitis vinifera* grape cultivars become infected with the disease, and vines degenerate rapidly to a point where fruit set is reduced and crop production becomes twenty percent (20%) or less than that of normal healthy vines of the same cultivar.

When *vinifera* scions are grafted onto standard phylloxera resistant rootstocks that are in general use, such as 'Harmony,' 'Couderc 1613,' 'Rupestris St. George' ('du Lot') and 'Ganzin 1', degeneration has not been prevented and oftentimes is exacerbated to a point where vines are virtually cropless.

The grapevine of this invention was selected from a cross made in 1948 between *Vitis vinifera* 'Almeria' and *V. rotundifolia* male No. 2. Initially, the selection was tested for phylloxera resistance and the success of those tests was reported in 1964. However, due to the difficulty in propagating the selection, as compared with the standard phylloxera-resistant rootstocks, 'VR 039-16' was not released. Interest in this vine was renewed when differential tolerance to infectious degeneration and *X. index* was observed. These observations led to the experiments which have determined the immunity of 'VR 039-16' to *X. index* feeding. Vines of 'VR 039-16,' when grafted with scions of susceptible vinifera cultivars such as 'Cabernet Sauvignon,' 'Chenin blanc,' and 'Carignane' and planted in infested soil have remained disease free and productive for at least seven (7) years. The tests were aided by a new serological technique which permits rapid detection of grapevine fanleaf virus in grapevine tissues. The technique is known as enzyme-linked immunosorbent assay (ELISA).

ELISA of tissues taken from experimental vines of 'VR 039-16' at various stages of growth gave proof that 'VR 039-16' was virtually free of infectious degeneration. Throughout the extended test period crop yield and vine growth were excellent, and the clusters and berries obtained on 'VR 039-16' stock demonstrated complete freedom of virus infection. The scions on the standard phylloxera-resistant rootstocks in the same tests as 'VR 039-16' displayed severe degeneration evidenced by low yields, smaller clusters and berries and reduced pruning weights.

'VR 039-16' was tested and has been found suitable for planting in vineyards infected with viruliferous nematodes in the important wine grape areas of Napa and San Joaquin Counties in California. The variety has been asexually reproduced by cuttings and although difficult to propagate, propagation has been improved by the application of rooting hormones.

In addition to its immunity to nematode feeding 'VR 039-16' is immune to phylloxera and resistant to most strains of root knot nematodes. It is distinguished from its companion rootstock 'VR 043-43' in that it is immune to phylloxera, whereas, 'VR 043-43' shows only tolerance. 'VR 039-16' differs from the standard phylloxera resistant rootstocks in that it is somewhat more difficult to propagate and is immune to vector feeding. Also, 'VR 039-16' is resistant to feeding by root knot nematodes, whereas 'St. George' and 'Ganzin 1' are not.

Definitive phenological and morphological characteristics of VR 039-16 are as follows:

FLOWERS

Flowers staminate with sterile pollen and poorly developed anthers. Indistinct but well-formed stigma on most flowers. Flower cluster form small, 4–6 cm long. Stamens moderately reflexed with tendency towards perfect flowering. Ovary small but well-formed. Sterile, with no fruit set.

LEAVES

Leaves deeply three to five lobed. Both inferior and superior sinuses are open. Margin distinctly and uniformly dentate. Older leaves slightly tomentose with tufted hairs that tend to dehisce. Younger leaves with soft long hairs on both upper and lower surface, more on upper surface. Mature leaves light to light yellow green. Vigorously growing shoot tips almost wooly white with tomentum.

TENDRILS

Tendrils, long, slender and well-formed, often longer than leaf blades; these are bifid, with discontinuous arrangement of vinifera type.

MATURE WOOD

Mature wood tan in color, with persistent bark and prominent lenticels. Nodes with septum.

TIME OF BLOOM

Blooms late, 12 to 14 days later than Semillon, 10% bloom at Davis on May 25, 1985.

We claim:

1. The new and distinct variety of grapevine rootstock herein described and illustrated and identified by the characteristics enumerated above.

* * * * *